US00PP27789P2

(12) United States Plant Patent
Zaiger et al.

(10) Patent No.: US PP27,789 P2
(45) Date of Patent: Mar. 21, 2017

(54) NECTARINE TREE NAMED 'POLAR KIST'

(50) Latin Name: ***Prunus persica* var. *nucipersica***
Varietal Denomination: Polar Kist

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 39 days.

(21) Appl. No.: 14/756,336

(22) Filed: Aug. 31, 2015

(51) Int. Cl.
*A01H 5/08* (2006.01)

(52) U.S. Cl.
USPC ..... Plt./188

(58) Field of Classification Search
USPC ..... Plt./188
See application file for complete search history.

*Primary Examiner* — June Hwu

(57) ABSTRACT

A new and distinct variety of nectarine tree. The following features of the tree and its fruit are characterized with the tree budded on 'Nemaguard' Rootstock (non-patented), grown on Handford sandy loam soil with Stone Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium size fruit.
3. Fruit with firm, crisp flesh with good eating quality.
4. Moderately juicy, which enhances flavor and eating quality.
5. Fruit with attractive red skin color.

1 Drawing Sheet

Botanical designation: *Prunus persica* var. *nucipersica*.
Variety denomination: 'Polar Kist'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually, reproduced by us in our experimental orchard located near Modesto, Stanislaus County, Calif.

PRIOR VARIETIES

Among the existing varieties of nectarine trees, which are known to us, and mentioned herein, 'Polar Light' Nectarine (U.S. Plant Pat. No. 16,858).

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was originated by us in our experimental orchard located near Modesto, Calif. as an open pollinated seedling selection from a seedling of unknown parentage. A large number of these open pollinated seedlings were grown and budded to older trees of 'Nemaguard' Rootstock (non-patented) to accelerate rapid fruit production. Under close and careful observation we recognized the desirable tree and fruit characteristics of the present seedling and selected it in 2006 for additional asexual propagation and commercialization.

ASEXUAL REPRODUCTION OF THE VARIETY

In 2006 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and a productive and regular bearer of medium size, white flesh, clingstone fruit. The fruit is further characterized by its attractive red skin color, good flavor and eating quality with good handling and storage quality. In comparison to the commercial variety 'Polar Light' Nectarine (U.S. Plant Pat. No. 16,858) the fruit of the new variety is approximately 7 days later in maturity.

DESCRIPTION OF PHOTOGRAPH

The accompanying color photographic illustration shows typical specimens of the foliage and fruit of the present new nectarine variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 9 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing necessary for desired market size fruit. Number of fruit set varies with climatic conditions during blooming period.

*Bearer*.—Regular, has had adequate fruit set 7 consecutive years. No alternate bearing observed.

*Fertility*.—Self fertile.

*Density*.—Medium dense, usually pruned to vase shape to increase air movement and sunlight to center of tree to enhance fruit color and health of fruit wood.

*Hardiness*.—Hardy in all stone fruit growing areas of California. Tree grown in USDA Hardiness Zone 9. Winter chilling requirement approximately 500 hours at or below 45° F.

Trunk:

*Size*.—Large. Average circumference 71.1 cm at 25.4 cm above ground on a 9 year old tree.

*Stocky*.—Medium stocky.

*Texture*.—Medium shaggy, roughness increases with age.

*Color*.—Varies from 10YR 4/2 to 10YR 3/2.

Branches:

*Size*.—Medium. Average circumference 22.6 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 14 in a 25.8 square cm section. Average length 4.8 mm. Average width 2.2 mm. Color varies from 10YR 5/6 to 10YR 4/6.

*Color*.—New growth varies from 5GY 6/8 to 5GY 5/8. Mature growth varies from 10YR 3/2 to 10YR 3/4, varies with age of growth.

Leaves:

*Size*.—Large. Average length 160.4 mm. Average width 43.1 mm.

*Form*.—Lanceolate.

*Apex*.—Acuminate.

*Base*.—Cuneate.

*Margin*.—Crenate.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.3 mm. Average width 1.6 mm. Longitudinally grooved. Surface — glabrous. Color varies from 5GY 7/6 to 5GY 6/6.

*Glands*.—Type — reniform. Size — large. Average length 1.3 mm. Average diameter 1.0 mm. Number varies from 3 to 5, average number 4. Located primarily on the base of the leaf blade and the upper portion of petiole. Color varies from 5GY 6/6 to 5GY 5/6.

*Stipules*.—Average number 2. Average length 10.0 mm. Edges pectinate. Color varies from 5GY 6/6 to 5GY 5/6.

*Color*.—Upper surface varies from 7.5GY 3/4 to 5GY 3/6. Lower surface varies from 7.5GY 4/4 to 7.5GY 4/6. Midvein color varies from 5GY 5/4 to 2.5GY 6/4.

Flower buds:

*Size*.—Large. Average length 18.6 mm. Average diameter 10.5 mm.

*Hardiness*.—Hardy with respect to California winters.

*Density*.—Light.

*Form*.—Elongated.

*Pedicel*.—Average length 5.3 mm. Average width 1.2 mm. Surface glabrous. Color varies from 5GY 8/6 to 5GY 7/10.

*Color*.—Varies from 5R 8/6 to 5RP 7/10.

Flowers:

*Blooming period*.—Date of First Bloom Feb. 4, 2015. Date of Petal Fall Feb. 14, 2015, varies slightly with climatic conditions.

*Size*.—Large, showy. Average height 21.0 mm. Average diameter 48.6 mm.

*Petals*.—Normally 5, alternately arranged to sepals. Size — large. Average length 23.0 mm. Average width 22.5 mm. Form — orbicular. Petal apex rounded. Petal base rounded to truncate. Margin — sinuate. Arrangement — free to slightly overlapping. Color varies from 5RP 9/2 to 5RP 8/6, fades with age of flower. Both upper and lower surfaces glabrous.

*Sepals*.—Normally 5, alternately arranged to petals. Size — large. Average length 8.8 mm. Average width 6.7 mm. Shape — triangular. Apex — triangular to rounded. Margin — entire. Color — upper surface varies from 7.5GY 6/10 to 7.5GY 5/10. Lower surface varies from 2.5R 3/6 to 2.5R 2/8. Upper surface glabrous. Lower surface pubescent.

*Stamens*.—Average number per flower 47. Average filament length 15.3 mm. On average the stamens are even with the height of the flowers. Filament color varies from N 9.5/(white) to 5RP 8/4. Anther color varies from 7.5R 4/12 to 5Y 8.5/10.

*Pollen*.—Self fertile. Color varies from 5Y 8/10 to 5Y 7/12.

*Pistil*.—Number — normally one. Surface glabrous. Average length 22.8 mm. Position of stigma an average of 1.1 mm above anthers. Color varies from 2.5GY 9/6 to 2.5GY 6/10.

*Fragrance*.—Slight.

*Color*.—Varies from 5RP 9/2 to 5RP 7/10.

*Pedicel*.—Average length 5.5 mm. Average width 1.5 mm. Color varies from 5GY 7/6 to 5GY 6/6. Surface glabrous.

*Number flowers per flower bud*.—Normally one.

Fruit:

*Maturity when described*.—Firm ripe, and ready for consumption.

*Date of first picking*.—May 25, 2015.

*Date of last picking*.—Jun. 4, 2015, varies slightly with climatic conditions.

*Size*.—Medium. Average diameter axially 61.4 mm. Average transversely in suture plane 69.5 mm. Average weight 164.7 grams, varies slightly with fertility of the soil, amount of thinning and climatic conditions.

*Form*.—Globose.

*Suture*.—Nearly smooth, some fruit with slight suture.

*Ventral surface*.—Smooth to slightly lipped.

*Apex*.—Rounded to slightly retuse.

*Base*.—Flat.

*Stem cavity*.—Rounded to slightly elongated in suture plane. Average depth 6.3 mm. Average diameter 7.7 mm.

Stem:

*Size*.—Small to medium. Average length 7.8 mm. Average diameter 3.5 mm.

*Color*.—Varies from 2.5GY 6/8 to 5GY 5/8.

Flesh:

*Ripens*.—Evenly.

*Texture*.—Firm, meaty, crisp.

*Fibers*.—Few, small, tender.

*Firmness*.—Good, comparable to other commercial nectarine varieties.

*Aroma*.—Slight.

*Amydgalin*.—Undetected.

*Eating quality*.—Good.

*Flavor*.—Good, mild and sweet. Good balance between acid and sugar.

*Juice*.—Moderate amount, enhances flavor.

*Acidity*.—Not available.

*Brix*.—Average Brix 14.0°, varies slightly with amount of fruit per tree and climatic conditions.

*Color*.—Varies from 2.5Y 8/2 to 7.5GY 8/2.

*Pit cavity*.—Average length 36.8 mm. Average width 23.6 mm. Average depth 10.9 mm. Color varies from 10Y 7/4 to 7.5Y 7/4.

Skin:

*Thickness*.—Medium.

*Surface*.—Smooth.

*Pubescence*.—Wanting.

*Tendency to crack*.—None.

*Color*.—Ground color varies from 7.5Y 9/2 to 7.5Y 9/4. Overspread with 7.5R 3/10 to 7.5R 2/8.

*Tenacity*.—Tenacious to the flesh.

*Astringency*.—Undetected.

Stone:

*Type*.—Clingstone, strong adherence to the flesh.

*Size*.—Medium. Average length 35.8 mm. Average width 22.6 mm. Average thickness 19.8 mm.

*Form*.—Ovoid.

*Base*.—Flat.

*Apex*.—Pointed. Average length 1.0 mm.

*Surface*.—Pitted throughout, pits vary from rounded to elongated.

*Sides*.—Unequal, one side extending further from suture plane.

*Ridges*.—Relatively smooth, extending from base to apex.

*Tendency to split*.—Slight.

*Color*.—Varies from 10YR 5/4 to 2.5Y 8/2 when dry.

Kernel:

*Size*.—Medium. Average length 17.5 mm. Average width 12.6 mm. Average depth 9.6 mm.

*Form*.—Ovoid.

*Viability*.—Partially viable, not all embryos fully developed.

*Skin color*.—Varies from 5Y 9/4 to 7.5Y 9/4.

Use:

*Dessert*.—Market — local and long distance.

Keeping quality: Good, held firm in cold storage for 2 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

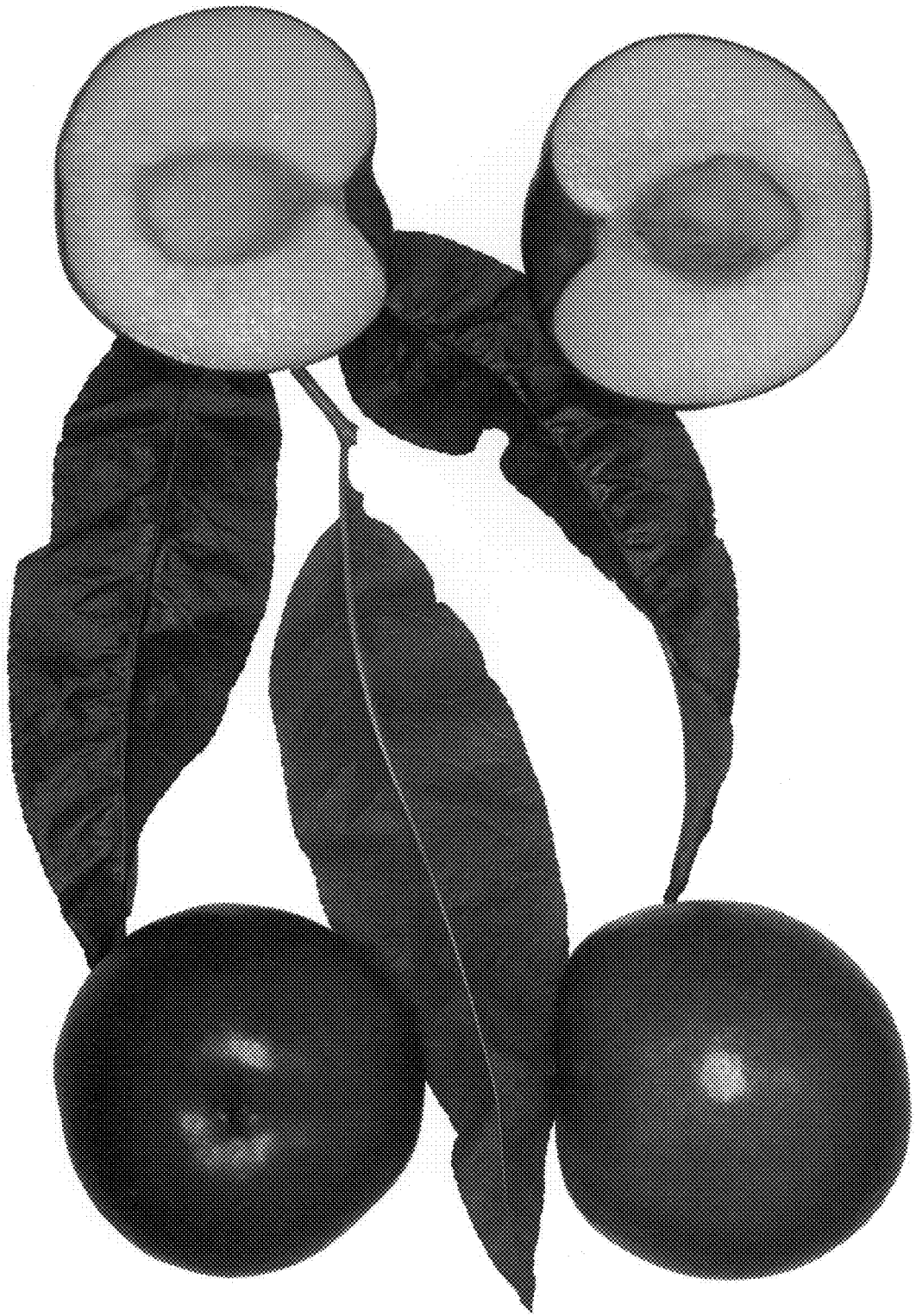

* * * * *